United States Patent [19]
O'Connell

[11] Patent Number: 5,590,431
[45] Date of Patent: Jan. 7, 1997

[54] STRETCHER FRAME CLAMP

[76] Inventor: Kevin R. O'Connell, Carter Notch Rd., Box 394, Jackson, N.H. 03846

[21] Appl. No.: 506,786

[22] Filed: Jul. 25, 1995

[51] Int. Cl.⁶ .................................................. A61F 5/04
[52] U.S. Cl. ..................... 5/658; 5/625; 602/34
[58] Field of Search .............. 602/32–35; 5/503.1, 5/658, 625, 629; 24/284; 403/335, 337, 338; 285/419

[56] References Cited

U.S. PATENT DOCUMENTS

| | | | |
|---|---|---|---|
| 885,243 | 4/1908 | Haas . | |
| 1,949,984 | 3/1934 | Walker | 403/337 X |
| 1,996,052 | 4/1935 | Allaire et al. | 128/84 |
| 2,079,617 | 5/1937 | Johnson | 128/84 |
| 2,150,314 | 3/1939 | Bell | 128/84 |
| 2,259,757 | 10/1941 | Longfellow | 602/34 |
| 2,297,861 | 10/1942 | Au Coin | 128/84 |
| 2,875,753 | 3/1959 | Sulmonetti | 128/84 |
| 3,033,198 | 5/1962 | Jensen | 602/33 |
| 3,381,684 | 5/1968 | Anderson | 128/68 |
| 3,850,165 | 11/1974 | Throner | 602/34 |
| 3,917,424 | 11/1975 | Zugel | 403/287 |
| 4,236,265 | 12/1980 | Carradine | 5/658 X |
| 4,547,092 | 10/1985 | Vetter et al. | 403/59 |
| 4,551,872 | 11/1985 | Reed | 602/34 X |
| 4,619,545 | 10/1986 | Kuttenbaum | 403/169 |
| 4,730,606 | 3/1988 | Leininger | 128/75 |
| 4,887,325 | 12/1989 | Tesch | 5/84 |

Primary Examiner—Michael F. Trettel
Attorney, Agent, or Firm—Devine, Millimet & Branch

[57] ABSTRACT

The invention comprises a novel stretcher frame clamp, which allows standard hospital-style traction components to be used in conjunction with ambulance cots or the like. In the preferred embodiment, the clamp comprises two clamp halves, which when joined together define an octagonal outer shaped clamping area. The octagonal outer shape of the clamping area is sized to adapt to octagonal tubing-based traction components. Each clamp half also has a recessed channel cut therein, which is of a shape and size so that when the clamp halves are joined together around a stretcher frame rail, the frame rail passes through the center of the frame clamp assembly and contacts the clamp assembly along the entire length of the frame rail section which passes therethrough. The clamp halves are held together to create the clamp assembly in a compressive fashion, so as to squeeze the stretcher frame rail as it passes through the clamp assembly. Thus, the clamp assembly is held rigidly in position on a stretcher frame rail and serves as the base to which hospital-style traction components are attached.

8 Claims, 3 Drawing Sheets

STRETCHER FRAME CLAMP

FIELD OF THE INVENTION

The present invention relates to the field of orthopedic traction. Specifically, the invention is directed to an apparatus and method for providing traction to a patient in an environment other than a special purpose orthopedic bed. In particular, the invention comprises a stretcher frame clamp which allows standard, hospital-style traction components to be rigidly attached to ambulance cots, hospital "gurneys", movable emergency room stretchers and the like.

BACKGROUND OF THE INVENTION

It is well known in the art to provide specialized treatment beds configured to accept orthopedic traction components. These beds are highly sophisticated and are generally found in orthopedic wards in major city hospitals. Although they can be found in more rudimentary form in almost any hospital facility. A large number of orthopedic traction components are manufactured and sold for use with these orthopedic treatment beds. These components allow physicians and the like to construct traction apparatus ranging from simple, in-line configurations to complex multi-access arrangements. However, while the state of the art related to the utilization of traction apparatuses in orthopedic ward settings is well developed, the need often arises to allow for a patient to be maintained in traction at locations other than an orthopedic ward in a hospital. One such time, when traction would be desired, is during the transport of a patient who has suffered a broken bone to a hospital where the broken bone can be properly treated.

Another use of the disclosed invention is in conjunction with emergency room beds, stretchers or gurneys. These types of beds are generally provided on wheels so that a patient being treated in an emergency room can be readily moved to an operating room, x-ray room, orthopedic ward, or the like. However, these beds are generally not configured to accept common orthopedic traction-related devices.

There are prior art references that disclose the use of traction apparatus in conjunction with movable beds. U.S. Pat. No. 4,236,265, which issued to Carradine on Dec. 2, 1980, is one such reference. This reference discloses the use of traction components in conjunction with a portable bed, cot or "gurney". However, the Carradine invention requires a specially-configured gurney, manufactured to accept the traction components.

U.S. Pat. No. 3,850,165, which issued to Throner on Nov. 26, 1994 discloses another "portable traction system". However, like the Carradine system, the Throner system is also a specially-adapted, orthopedic-style bed.

None of the prior art references disclose the applicant's novel apparatus, which allows standard, hospital-style traction components to be utilized in conjunction with both standard, off-the-shelf, ambulance-style cots and standard emergency room style movable stretchers or gurneys.

SUMMARY OF THE INVENTION

The invention comprises a novel stretcher frame clamp, which allows standard hospital-style traction components to be used in conjunction with ambulance cots or the like. In the preferred embodiment, the clamp comprises two clamp halves, which when joined together define an octagonal outer shaped clamping area. The octagonal outer shape of the clamping area is sized to accept octagonal tubing-based traction components. Specifically, a standard octagonal clamping unit would be joined to the stretcher frame clamp and would serve as the base for an orthopedic traction set up. The stretcher frame clamp has first and second ends, each of which has an enlarged shoulder area. These shoulders provide sufficient room and additional strength for holding means to pass therethrough and hold the clamp sections together in a rigid position on the stretcher frame or the like.

Each clamp half has a substantially flat face, which is opposite a like face of the other clamp half when the clamp halves are joined to create the clamp assembly. Centrally located and disposed in each flat face, along the longitudinal axis of each clamp half, is a recessed channel. These channels are also directly opposite each other when the stretcher frame clamp halves are joined into the clamp assembly such that, when the halves are assembled, a centrally located through channel is created along the longitudinal axis of the clamp assembly. The through channel can be configured in various shapes and sizes to accommodate varying shapes and sizes of the stretcher, cot, or bed frame for which the clamp assembly is especially adapted.

The clamp is affixed to the stretcher, or the like, by placing each clamp half on opposite sides of the tubular stretcher frame member such that the frame member passes through the longitudinally disposed through channel in the clamp assembly. The clamp is then held in position through the use of four screw means, which are tightened to clamp in position. In order to provide maximum clamping power, the mating faces of the clamp halves are machined to provide clearance when the clamp halves are combined and tightened in position around the stretcher frame or the like. Thus, the entire clamping power is directed from the clamp assembly to the stretcher frame along the through channel, which holds the clamp assembly rigidly in position.

DETAILED DESCRIPTION OF THE DRAWINGS

Figure 1:
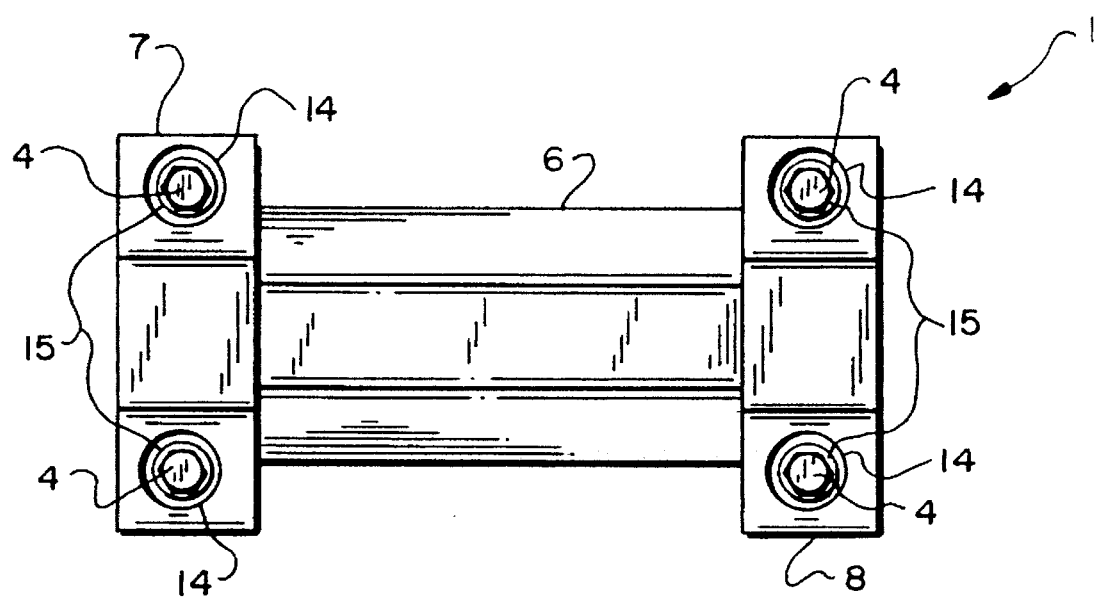
FIG. 1 is a side view of one stretcher frame clamp half.
Figure 2:
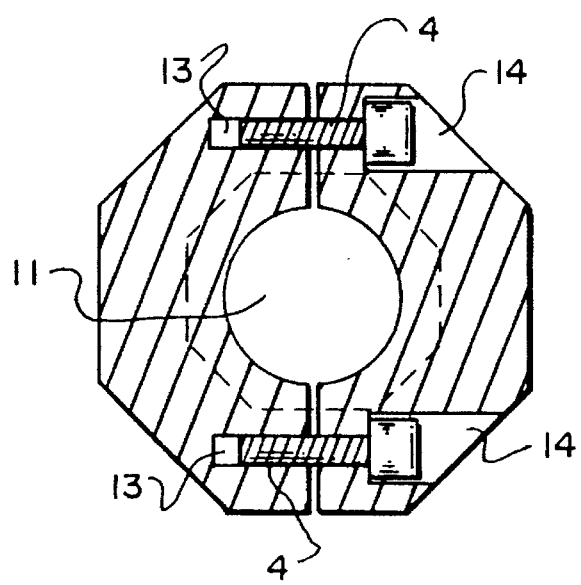
FIG. 2 is a sectional end view of the stretcher clamp showing the compression screws in their tightened position.
Figure 3:
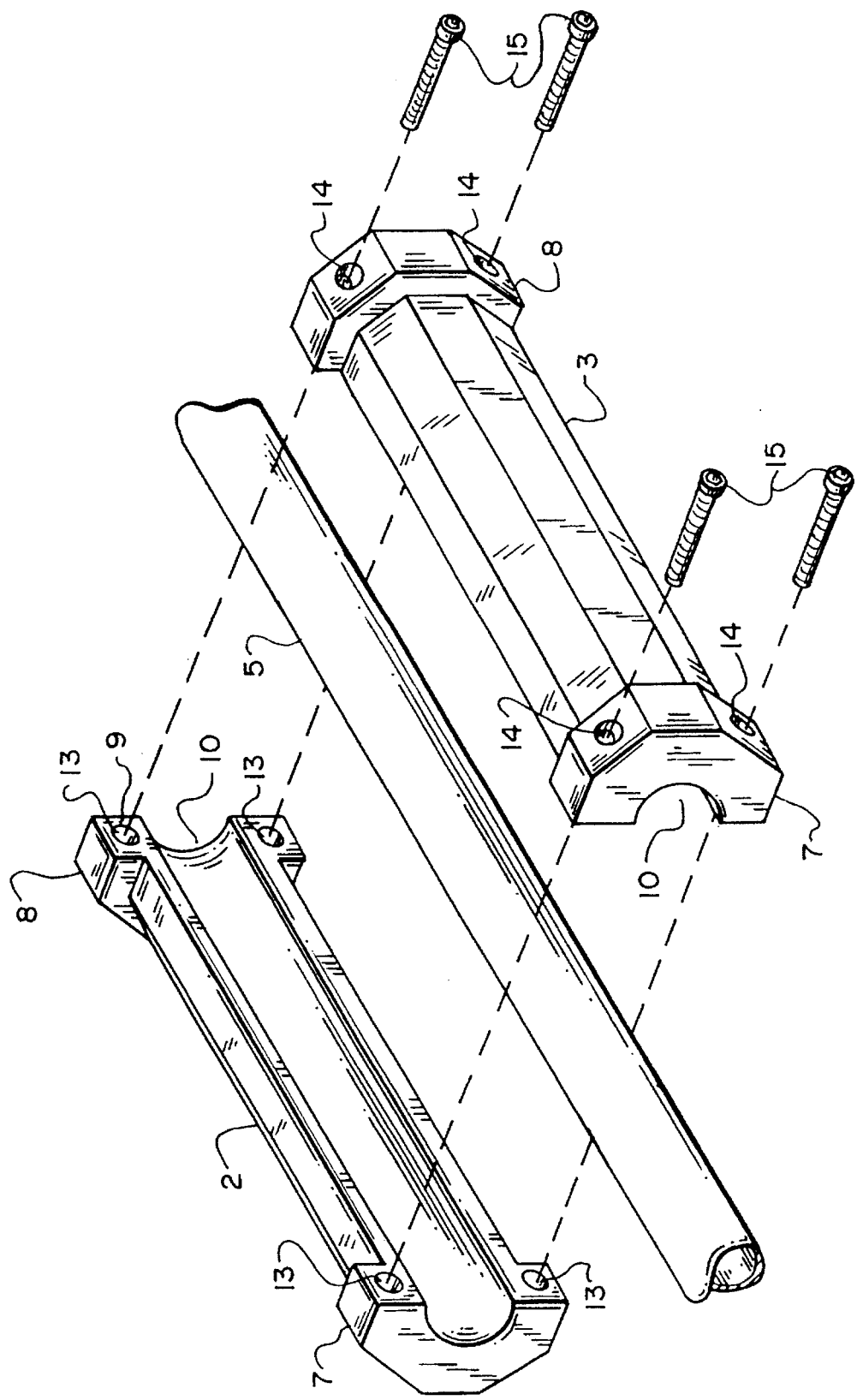
FIG. 3 is an exploded perspective view of the clamp assembly, showing its component parts and its relationship to a tubular stretcher frame rail.
Figure 4:
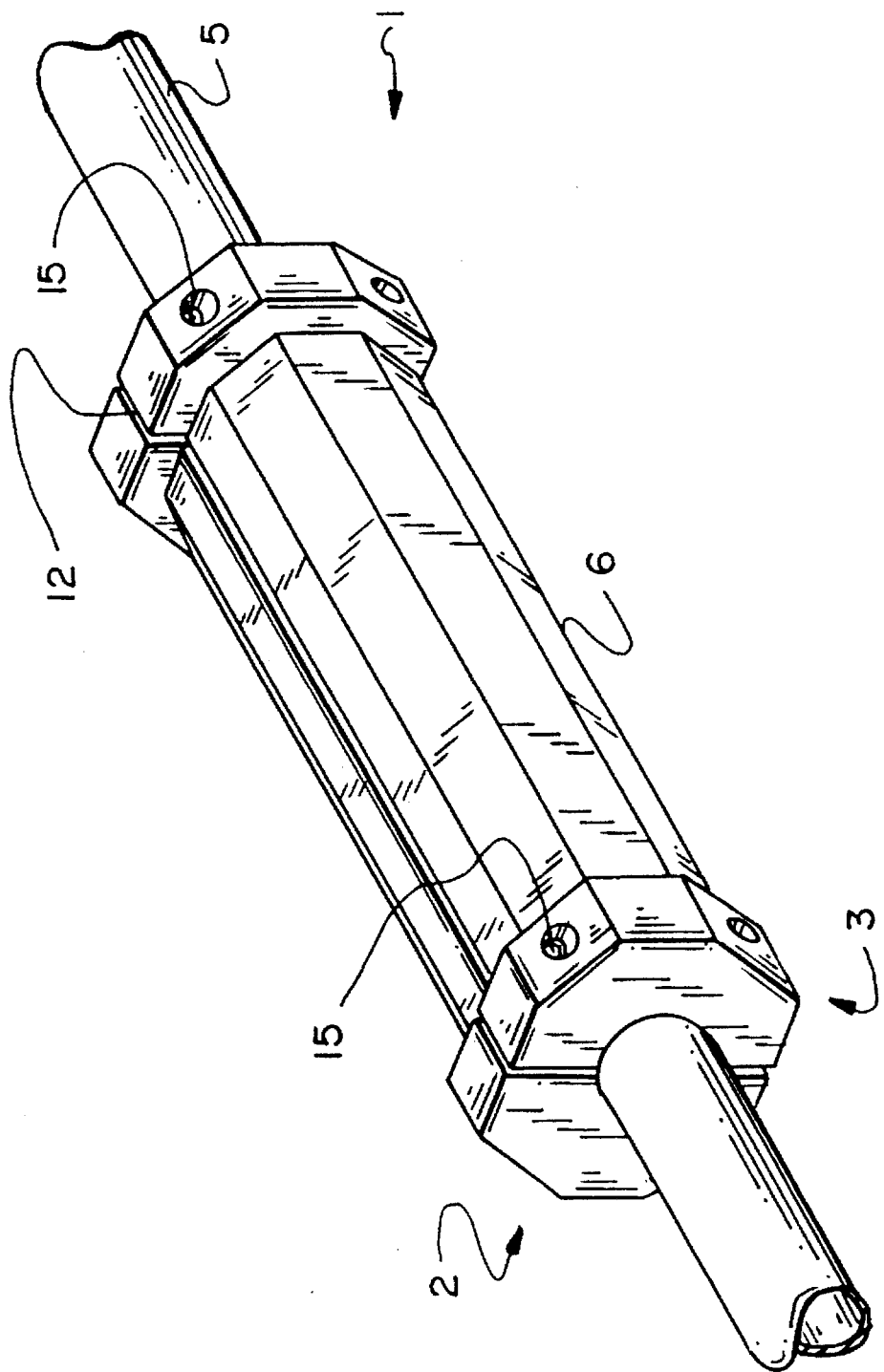
FIG. 4 is a perspective view of the clamp in position on the stretcher frame.

Referring now to the figures, there can be seen a stretcher frame clamp, generally designated 1. In the embodiment described, the stretcher frame clamp comprises two clamp halves 2 and 3 and a holding means 4 for joining the clamp halves together as a unit and firmly in position on a stretcher or bed frame rail 5. However, it is envisioned that embodiments can utilize more than two clamp halves, which embodiments are contemplated as being within the spirit and scope of the disclosed invention.

When the clamp halves are joined, they create a clamping area 6, which has an octagonal outer cross section. The octagonal outer cross section is selected and sized to allow standard hospital-style orthopedic traction components to be rigidly attached to the gripping area, which in turn is rigidly attached to a stretcher frame or the like. Octagonal tubing based traction components are manufactured by a number of medical device manufacturers. However, the most popular components are manufactured by the Zimmer Patient Care Division of Bristol-Myers Squib Corporation ("Zimmer"). In particular a Zimmer octagonal clamping unit would be clamped to the stretcher frame clamp assembly in order to provide the base for a traction apparatus to be utilized with a patient occupying the stretcher or the like. The traction apparatus would be constructed according to standard teachings in the art, which could utilize a number of base clamps. Thus, it is envisioned that a single stretcher or like movable bed would incorporate more than one stretcher frame clamp assembly and could incorporate four, six, or even eight assemblies at various locations around the stretcher frame.

At each end of the clamping area 6, the clamp assembly comprises raised shoulders 7 and 8. These shoulders allow the traction components to be easily located on the stretcher frame clamp assembly along its longitudinal axis and provide sufficient room and additional strength for holding means 4 to pass therethrough and hold the clamp halves together in a rigid position on the stretcher frame or the like. While the figures show shoulders that are also substantially octagonal in cross section, this was chosen more as a matter of manufacturing convenience and is not critical to the inventive concept disclosed herein.

The first clamp half has a substantially flat face 9, which opposes a like face on the second clamp half when the clamp halves are positioned around the stretcher frame or the like to create the clamp assembly 1. Centrally located, along the longitudinal axis of each flat face is a channel 10 recessed in said flat face. The size and shape of each recessed channel 10 is sufficient so that when the clamp halves are joined together, a longitudinally disposed through channel 11 is created in the clamp assembly, which is substantially the same shape and size as the shape and size of the stretcher frame tubing 5 for which the clamp assembly 1 is especially adapted. Since many ambulance cots and emergency room stretchers are manufactured with cylindrical, extruded tubular frame rails, the disclosed invention is particularly adapted to be used in conjunction with such configurations. In fact, cylindrical, extruded tubular stretcher frames provide a unique challenge to create a clamp assembly that can be rigidly secured in position with sufficient gripping power to prevent the assembly from rotating about the stretcher frame. This is especially critical since a patient suffering from a broken limb will generally be using such an apparatus, and any unwanted movement of the broken limb could result in additional injuries or complications to the trauma site.

Thus, in order to ensure maximum gripping power of the clamp assembly where it contacts the stretcher or bed frame rail, the flat face of each clamp half is machined to provide sufficient clearance 12 between the flat faces when the clamp halves are joined in position about the stretcher frame so that the entire gripping force being exerted by the clamp assembly's holding means is directed to the walls of the stretcher frame tubing where it contacts the walls of the recessed channels 10 in each clamp half. Generally, clearances between 0.015 and 0.030 inches have proven to be adequate to ensure maximum gripping power. In fact, clamps utilizing these clearances provide gripping power that exceeds the structural limitation of the tubular traction components.

The raised shoulders 7 and 8 at either end of the clamping area provide sufficient clearance and strength for holding means 4 to attach therewith to rigidly join the clamp halves together in position and also to provide a sufficient compressive force upon the stretcher frame tubing 5 to hold the clamp assembly 1 in position and preclude rotation of the clamp assembly around the stretcher frame tubing. The holding means itself comprises a plurality of threaded bores 13 in the first stretcher frame clamp half 2. The threaded bores are generally located in the flat face 9 at the larger shoulders and are oriented substantially perpendicular to the mating face. The second stretcher frame clamp half 3 comprises a like number of countersunk through bores 14. These through bores are also located in the shoulders 7 and 8 of the second clamp half 3, perpendicular to its flat face 9. These through bores are also located so that when the clamp halves are joined to form the clamp assembly, a plurality of fasteners 15, which may take the form of machine screws or the like, can be inserted through the through bores in the second clamp half and engage the threads of the threaded bores in the first clamp half directly opposite their respective through bores.

In order to use the clamp assembly, the clamp halves are located circumferentially around a stretcher frame rail in the desired location. The required number of machine screws, which in the preferred embodiment is four, are then inserted through the through bores in the second clamp half and are threaded into the threaded bores in the first clamp half. The screws are then tightened. This tightening of the screws compresses the clamp assembly around the stretcher frame rail as the rail passes through the recessed channel in the clamp assembly.

Various other changes coming within the scope of the invention may suggest themselves to those skilled in the art: hence, the invention is not limited to the specific embodiment shown or described, but the same is intended to be merely exemplary. It should be understood that numerous other modifications and embodiments can be devised by those skilled in the art that will fall within the spirit and scope of the principles of the invention.

What is claimed is:

1. A stretcher frame clamp assembly for adapting orthopedic traction components to a movable bed unit having tubular frame rails, said assembly comprising: a plurality of clamp sections adapted to be joined together to surround a tubular frame rail section, said clamp assembly comprising a clamping area having a substantially octagonal outer cross section, and a means for joining said clamp sections in such a manner so as to firmly grip said bed unit frame rail section where it passes through said clamp assembly and prevents said assembly from rotating around said frame rail section.

2. The stretcher frame clamp assembly as claimed in claim 1, wherein said clamp sections further comprise enlarged shoulder sections at first and second ends of said clamp sections, said shoulder sections adapted to accept said means for joining said clamp sections into said clamp assembly.

3. The stretcher frame clamp assembly as claimed in claim 2, wherein said clamp assembly comprises first and second clamp sections, each said section having a substantially flat face.

4. The stretcher frame clamp assembly as claimed in claim 3, wherein said means for joining said clamp sections into said clamp assembly comprises a plurality of threaded bores disposed in said first clamp section perpendicular to its flat face, a plurality of countersunk through bores is said second clamp section, said through bores perpendicular to its flat face and aligned substantially with said threaded bores in said first section and a plurality of fasteners, which pass through said through bores and engage said threaded bores, said fasteners being tightened to rigidly secure said clamp assembly in its desired position on said frame rail section.

5. The stretcher frame clamp assembly as claimed in claim 4, wherein said tubular frame rails have a circular cross section.

6. The stretcher frame clamp assembly as claimed in claim 4, wherein said tubular frame rails have a rectangular cross section.

7. The stretcher frame clamp assembly as claimed in claim 1, wherein said movable bed unit is an ambulance style cot.

8. The stretcher frame clamp assembly as claimed in claim 1 wherein said movable bed unit is an emergency room stretcher.

* * * * *